United States Patent
Connolly et al.

(10) Patent No.: US 11,090,058 B2
(45) Date of Patent: *Aug. 17, 2021

(54) SYSTEMS AND METHODS FOR DELIVERY OF GEL EMBOLICS

(71) Applicant: Boston Scientific Scimed, Inc., Maple Grove, MN (US)

(72) Inventors: Joseph Michael Connolly, Minneapolis, MN (US); Gary Pederson, Albertville, MN (US); Mary-Claire Anderson, St. Louis Park, MN (US); Patrick A. Haverkost, Corcoran, MN (US); David Raab, Minneapolis, MN (US); Mark Smith, Coon Rapids, MN (US)

(73) Assignee: Boston Scientific Scimed, Inc, Maple Grove, MN (US)

( * ) Notice: Subject to any disclaimer, the term of this patent is extended or adjusted under 35 U.S.C. 154(b) by 254 days.

This patent is subject to a terminal disclaimer.

(21) Appl. No.: 16/292,621

(22) Filed: Mar. 5, 2019

(65) Prior Publication Data

US 2019/0201001 A1     Jul. 4, 2019

Related U.S. Application Data

(63) Continuation of application No. 15/089,084, filed on Apr. 1, 2016, now Pat. No. 10,265,078.

(60) Provisional application No. 62/141,536, filed on Apr. 1, 2015.

(51) Int. Cl.
     *A61B 17/12* (2006.01)

(52) U.S. Cl.
     CPC .... *A61B 17/1219* (2013.01); *A61B 17/12022* (2013.01); *A61B 17/12113* (2013.01); *A61B 17/12159* (2013.01); *A61B 17/12172* (2013.01); *A61B 17/12186* (2013.01); *A61B 2017/1205* (2013.01); *A61B 2017/12054* (2013.01); *A61B 2017/12063* (2013.01); *A61B 2017/12068* (2013.01)

(58) Field of Classification Search
     CPC ........ A61B 17/12022; A61B 17/12133; A61B 17/12159; A61B 17/12172; A61B 17/12186; A61B 17/1219; A61B 2017/1205; A61B 2017/12054; A61B 2017/12063; A61B 2017/12068
     See application file for complete search history.

(56) References Cited

U.S. PATENT DOCUMENTS

| 10,265,078 | B2 * | 4/2019 | Connolly | ......... A61B 17/12172 |
| 2005/0267528 | A1 * | 12/2005 | Ginn | ............... A61B 17/12172 606/214 |
| 2014/0031858 | A1 * | 1/2014 | Bhagchandani | ... A61B 17/1214 606/200 |
| 2014/0277074 | A1 * | 9/2014 | Kaplan | ............ A61B 17/12122 606/198 |

* cited by examiner

*Primary Examiner* — Jocelin C Tanner
(74) *Attorney, Agent, or Firm* — Kacvinsky Daisak Bluni PLLC

(57) ABSTRACT

Delivery systems for liquid embolics and methods of using them are disclosed. The devices generally include a catheter and one or more retention elements to limit migration of the liquid embolic to non-target sites.

20 Claims, 3 Drawing Sheets

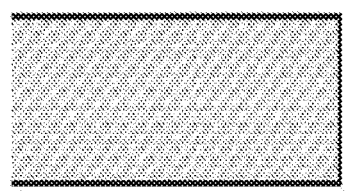
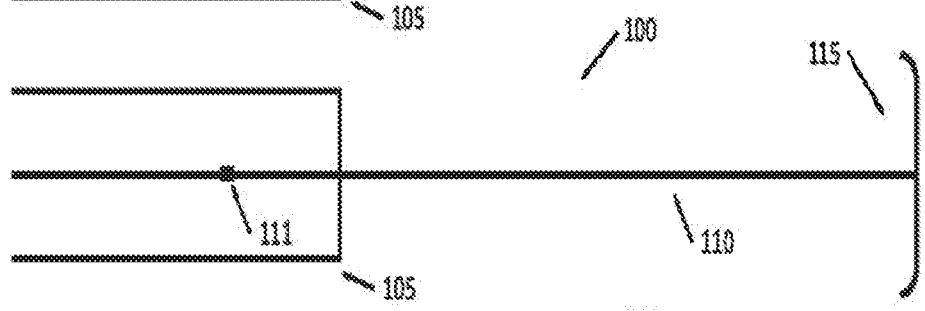
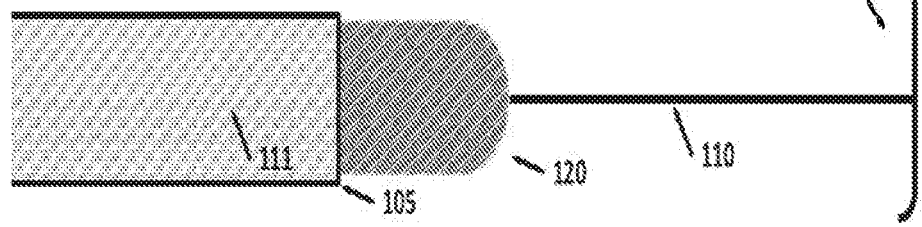
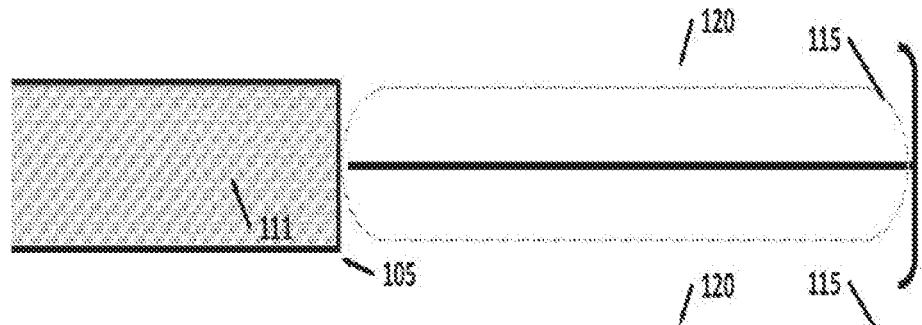
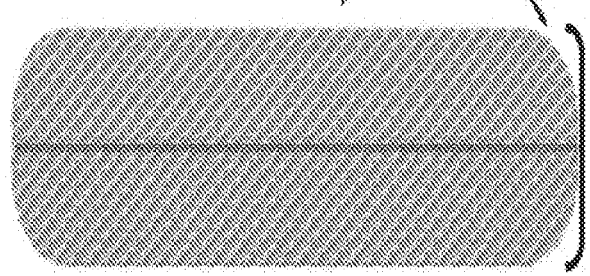

SYSTEMS AND METHODS FOR DELIVERY OF GEL EMBOLICS

CROSS-REFERENCE TO RELATED APPLICATIONS

This application claims the benefit of priority under 35 USC § 119 to U.S. patent application Ser. No. 15/089,084 filed Apr. 1, 2016, which claims priority to U.S. Provisional Patent Application Ser. No. 62/141,536, filed Apr. 1, 2015, both of which are incorporated by reference herein in their entirety and for all purposes.

FIELD OF THE INVENTION

This application relates to the field of medical devices. More particularly, the application is related to devices and methods for the occlusion of blood vessels and/or the delivery of drugs to patients.

BACKGROUND

Embolization involves the partial or complete occlusion of blood vessels, limiting the flow of blood therethrough. The intentional occlusion of blood vessels ("therapeutic embolization") may be used to treat a variety of vascular and non-vascular conditions including cerebral and peripheral aneurysms, arteriovenous malformation, and uterine fibroids and to reduce blood flow to solid tumors including liver tumors. Embolization may be achieved by any number of means, including through the use of polymer microspheres, metal coils or plugs and liquid embolic materials.

In a typical embolization procedure, local anesthesia is first given over a common artery or vein. The artery or vein is then punctured and a catheter is inserted and fluoroscopically guided into the area of interest. An angiogram is performed by injecting contrast agent through the catheter, thereby visualizing the portion of the vascular tree downstream of the distal end of the catheter. Once the catheter is positioned in a site where deposition of an embolic agent is desired, the composition or agent is deposited through the catheter. The embolic agent is generally selected based on the size of the vessel to be occluded, the desired duration of occlusion, and/or the type of disease or condition to be treated, among others factors. Following delivery of the embolic agent to the site within the vessel to be occluded, a follow-up angiogram can be performed to determine the specificity and completeness of the occlusion.

In many common embolic procedures, including sandwich embolization of splanchnic aneurysms, sandwich embolization of gastrointestinal bleeds, embolization of vessels to treat varioceles or pelvic congestion syndrome, and embolization to arrest hemorrhage after trauma, embolization is desired along of a length of blood vessel, rather than at a focal point. However, embolic coils, which are most commonly used in embolization procedures, are optimally used in focal embolization applications. In practice, users may use multiple embolic coils to pack and fill the length of the vessel, but this approach is time- and material-intensive, as many coils must each be placed individually, increasing the costs of such procedures.

Liquid and swellable embolics have recently emerged as a potential alternative to coil-packing procedures. Throughout this disclosure, the terms "liquid embolics," "gel embolics" and "swellable embolics" are used interchangeably to refer to (a) flowable polymerizing embolic materials, which include TRUFILL® n-Butyl Cyanoacrylate (n-BCA) (Codman & Shurtleff, Inc., Raynham, Mass.) and ONYX® ethylene vinyl alcohol copolymer (EVOH) (ev3 Endovascular, Inc., Plymouth, Minn.), as well as (b) absorbent or superabsorbent polymer embolics, such as collagen occlusive plugs These materials can be expensive (up to $2,500 per mL in the case of EVOH embolics) and, when deployed in vessels with relatively high flow rates, may be prone to migration and embolization of non-target areas. To prevent such migration, practitioners may deploy coils on the proximal and/or distal ends of a region being embolized, in order to reduce blood flow thereto. This approach, however, also requires multiple steps, and may require the use of multiple catheters, particularly when using liquid embolics (such as n-BCA) solidify within the catheter, necessitating the placement of a new catheter if deployment of an embolic coil proximal to the already polymerized embolic mass is desired.

Another alternative to packing vessels with conventional embolic coils and/or liquid embolics is to use multiple hydrogel-coated embolic coils, such as the AZUR™ coil (Terumo Medical Corporation, Somerset, N.J.); these coils expand radially when exposed to aqueous environments, allowing them to occupy more space than conventional embolic coils having an equivalent pre-deployment diameter. Even so, procedures involving these devices will typically require placement of multiple coils, and will thus involve greater complexity and expense than interventions which require only a single deployment step.

SUMMARY OF THE INVENTION

The present invention, in its various aspects, addresses the shortcomings of existing coil and liquid embolics, and provides systems and methods for single-step delivery of embolics across a vascular length, rather than at a focal point.

In one aspect, the present invention relates to a system for treating a patient that includes a catheter, one or more retention elements slidably disposed within the catheter, and an embolic material that is flowable through, or slidably disposed in, a lumen of the catheter. The system also optionally includes an elongate body connected to the retention element(s), such as a shape memory wire, which wire in turn can include a detachable link such as an electrolytically several segment, a mechanical link, and a thermally severable segment. The retention element, which is generally (but not necessarily) moveable between a compressed configuration with a first diameter and an expanded configuration with a second, larger diameter, may have a spiral shape or a plurality of cross members (among other structures) and may be substantially planar when unconstrained, or it may form a more 3-dimensional structure. In some embodiments, the system includes two retention elements, one positioned proximally to the embolic material, the other distally, and optionally includes (i) a pushrod slidably disposed within the catheter and proximally to the most proximal retention element, and/or (ii) a retention element extending between the retentive elements and connecting them. In some instances, the embolic material absorbs water and/or forms a gel. These systems are useful in medicine, particularly in embolization of body lumens, and more particularly in vascular embolization procedures. An exemplary procedure utilizing such a device includes inserting the distal end of the catheter into a blood vessel, advancing the retention element distally from the catheter into the blood vessel, and disposing the embolic material proximally to the retention element through the catheter.

In another aspect, the present invention relates to a system for treating a patient that includes a catheter, an embolic material that is slidably disposed within the lumen of the catheter with first and second retention elements disposed proximally and distally about the embolic material, respectively, and a pushrod that slides within the catheter and is positioned proximally to the first retention element. The embolic material preferably (but not necessarily) absorbs water and/or forms a gel, and it may include collagen or another polymer, for example as a superabsorbent polymer plug.

In yet another aspect, the present invention relates to a method for treating a patient that includes a step of forming an occlusive structure within a blood vessel of a patient. The structure generally includes an expandable implant and a polymer plug contacting the implant, which plug includes or is formed by a liquid embolic material and/or a superabsorbent polymer material. The implant can include one or more retentive elements having structures—and in structural relationships to the plug—as described above.

DRAWINGS

Aspects of the invention are described below with reference to the following drawings in which like numerals reference like elements, and wherein:

FIG. 1A through 1E shows schematic views of delivery systems according to certain embodiments of the invention in various stages of deployment.

FIG. 2A through 2C shows schematic views of retention elements according to certain embodiments of the invention, while

Unless otherwise provided in the following specification, the drawings are not necessarily to scale, with emphasis being placed on illustration of the principles of the invention.

DETAILED DESCRIPTION OF THE PREFERRED EMBODIMENTS

Figure 2A:
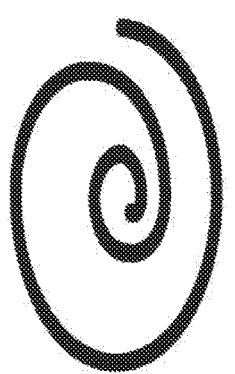
Figure 2B:
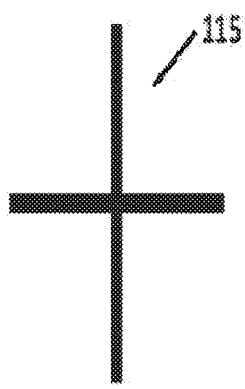
Figure 2C:
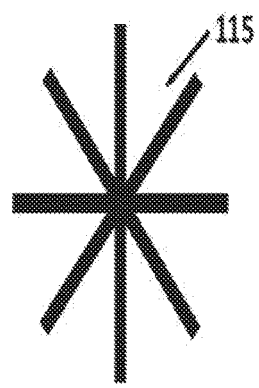

Turning to FIG. 1, an exemplary delivery system 100 according to one group of embodiments of the present invention comprises a catheter 105 and, slidably disposed within the catheter 105, a shape memory wire 110 that includes a retention structure 115 at its distal end. The retention structure 115 is, generally, radially compressible and expandable, to permit its insertion through a relatively narrow-gauge catheter bore to at least partially occlude a larger-diameter blood vessel. In general, the systems and methods of the present invention will be used in arteries ranging from 2-8 mm in diameter and veins ranging from 1-10 mm in diameter. The retention structure 115 can have any suitable shape to achieve such radial compression/expansion and, when expanded, to impede or prevent the flow of viscous materials such as liquid embolics and/or to prevent or limit migration of superabsorbent polymer embolic plugs. These shapes include, without limitation, a spiral shape (as shown in FIG. 2A) or a cruciate shape (shown in FIGS. 2B-C) comprising any suitable number of cross-members, including two, four, six, eight, etc.). The retention structure 115 also optionally includes a covering, such as an electrospun fiber matrix, comprising a polymer such as polytetrafluoroethylene (PTFE), expanded PTFE, polyethylene terephthalate (PET), polyvinylidene fluoride (PVDF), and the like.

Wire components of the delivery system 100, including the shape memory wire 110 and the retention element 115, are preferably made of a shape memory alloy such as nitinol, though other materials can be used such as stainless steel, shape-memory polymers, platinum, or poly-lactic acid (PLA) and/or poly-lactic-co-glycolic acid (PLGA). If a coating is used, it may be hydrophilic (e.g. Bioslide™ hydrophilic coating, Boston Scientific, Marlborough, Mass.), or hydrophobic (e.g. polytetrafluoroethylene (PTFE), silicone). The shape memory wire 110 and/or retention element 115 can also include an iodinated coating and/or a discrete fluoroscopic marker such as a platinum, palladium or tungsten band or other marker. If a severable link or joint is used, it can take any suitable form, including electrolytically severable links, thermally severable links, frangible links, and mechanical joints such as knotted tethers, male and female screw-ends, ball and socket mechanisms, etc. Exemplary detachment mechanisms for medical implants are described in, inter alia, U.S. Pat. No. 5,250,071 (describing interlocking clasp mechanisms incorporating complementary male and female ends), U.S. Pat. No. 5,354,295 (describing electrolytically severable core wires), U.S. Pat. No. 6,059,779 (describing annular return electrodes disposable about electrolytically severable core wires), and US pre-grant publication no. 20090177261 (describing detachment mechanisms utilizing materials that change shape in response to the application of heat or electrical energy, including synthetic polymers). Each of the foregoing references is hereby incorporated by reference in its entirety and for all purposes.

Retention elements 115 are shown in the drawings as being substantially planar, but other 3-dimensional shapes are used in various embodiments, including without limitation multiple spirals in multiple planes, birds-nest shapes, etc. The retention element 115 may also comprise a mesh and/or a textured surface to facilitate adhesion to the vessel wall. And, although the retention element 115 is described above as generally self-expanding, it can be, alternatively or additionally, expandable by means of a separate device or element, or by the application of an external stimulus such as the application of current or heat (e.g. expanding in response to a temperature change when inserted into the body) or may be physically expanded by a superabsorbent polymer plug as it expands in situ. In addition, in some embodiments, the retention element 115 is a detachable balloon.

In use, the delivery system 100 is used to deliver a liquid embolic or superabsorbent plug 120 into a blood vessel, according to a process generally illustrated in FIGS. 1A-E. The process begins with the insertion of the catheter 105 into the patient's vasculature, such that a distal end of the catheter 105 is proximate to, or within, a length of blood vessel where occlusion is desired. When the catheter 105 is positioned, the shape memory wire 110 is extended distally through a distal aperture of the catheter 105 and into the vessel. As it is extended, the retention element 115 at the distal end of the shape memory wire 110 preferably expands radially outward to contact an interior wall of the blood vessel. In preferred embodiments, the catheter 105 is positioned so that the retention element 115 is at or near its intended deployment site, then the catheter 105 is retracted, unsheathing the retention element 115 and the embolic material 110. Thereafter, a liquid embolic 120 is flowed through the catheter into the space defined by the distal end of the catheter 105 and the retention element 115. The liquid embolic 120 can be any material that polymerizes, cross-links, viscifies, or otherwise changes from a liquid to a gel or solid in situ (which processes are referred to throughout this application, for ease of presentation, as "hardening") following deployment into a blood vessel, such as n-BCA or EVOH.

After the liquid embolic 120 has hardened, the shape memory wire 110 is optionally severed, such that the retention element 115 and a distal portion of the wire 110 remain in place and attached to the embolic material 120 so as to form, together with the embolic material 120, an indwelling implant. Severing of the shape memory wire 110 is facilitated, in preferred embodiments, by the use of a severable link or joint 111, which can be a mechanically, electrolytically or thermally severable structure formed in the shape memory wire. In some alternative embodiments, however, the wire 110 is simply retracted back into the catheter 105 through the hardened embolic material 120; in these instances, retraction may be facilitated by a lubricious, hydrophobic or other coating on the wire 110, which coating prevents the wire from sticking to and disrupting the hardened embolic 120. Retraction of the shape memory wire 110 through the plug is also optionally facilitated by the use of a multi-lumen catheter 105, and the positioning of the shape memory wire 110 in a first lumen while the liquid embolic 120 is flowed through a second lumen. The second lumen can, also optionally, be larger in diameter than the first lumen, and the first lumen can also optionally be laterally offset from a central axis of the catheter 105, thereby placing the shape memory wire 110 adjacent to the wall of the blood vessel when deployed.

Figure 2D:
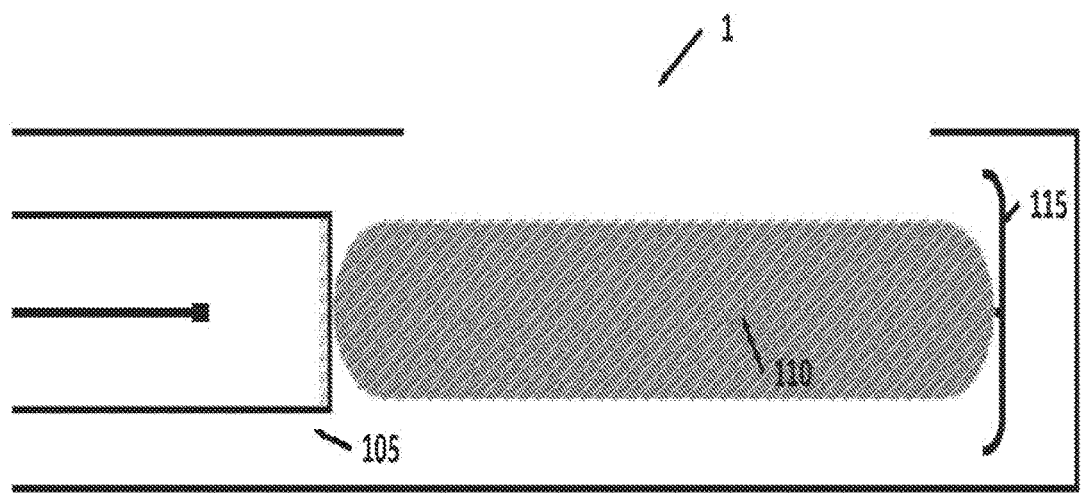
FIG. 2D shows a schematic view of a delivery system according to the invention in use in a procedure to occlude a blood vessel having a disrupted wall.

Delivery systems according to these embodiments may be particularly useful in embolization procedures for stopping hemorrhage, as shown in FIG. 2D. An exemplary deployment procedure for these applications is similar to the exemplary procedure described above with these additional considerations: the distal end of the catheter 105 is positioned proximate to (e.g. just proximal of) a disruption 1 in the wall of the blood vessel to be embolized, then the shape memory wire 110 is extended across a length of the blood vessel that spans the disruption 1, so that the retention element 115 is positioned distal to the disruption 1. With the delivery system so positioned, the liquid embolic 120 is flowed into the vessel so as to occlude the length of the vessel comprising the disruption 1, and the procedure continues as described above. Alternatively, the delivery system can be positioned proximally to (i.e. upstream of) the disruption 1, so that the deployment of the liquid embolic 1 interrupts blood flow to the disruption 1. Delivery system 100 is also useful more generally in procedures in which the target vasculature is not "end-organ," and downstream, non-target embolization is possible.

Figure 3A:
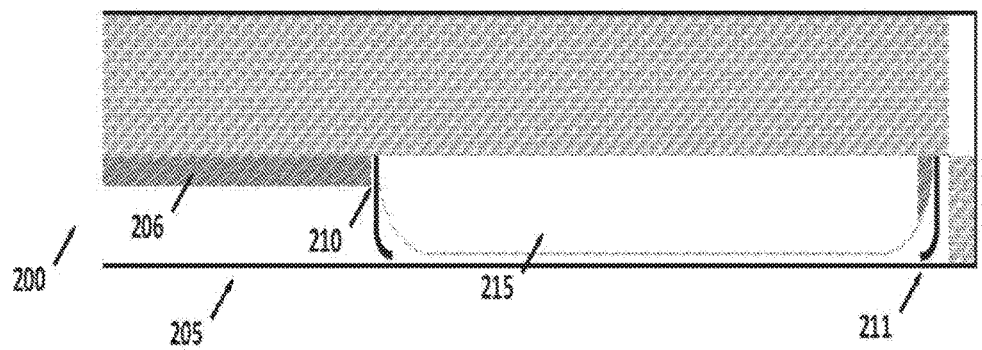
FIG. 3A through 3C shows schematic views of delivery systems according to certain embodiments of the invention in various stages of deployment.
Figure 3B:
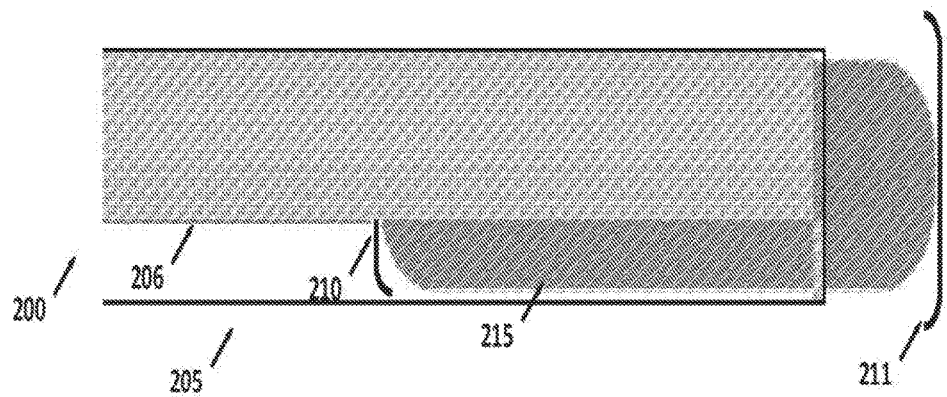
Figure 3C:
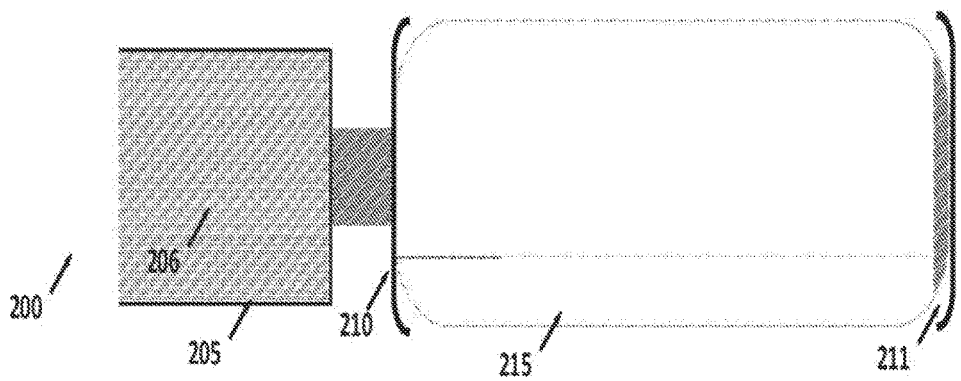

A second group of preferred embodiments, shown in FIG. 3 A-C, also utilize a catheter 205, but omit the shape memory wire in favor of first and second retentive elements 210, 211 which are placed about the proximal and distal ends of a bolus of embolic material 215. Each of the retentive elements 210, 211 and the embolic material 215 are slidably disposed within the catheter 205, which optionally includes a pushrod 206 to apply force to the proximal retention element 210 and the embolic material 215. When a pushrod 206 is used, it is optionally reversibly attached to the proximal retention element 210 by means of interlocking arms, a screw, or any other suitable means.

In a typical embolization procedure using a delivery system according to this group of embodiments, the catheter 205 is positioned so that its distal end is adjacent to, or within, a length of blood vessel in which embolization is desired. For instance, in the sequence shown in FIG. 3A-C, the distal end of the catheter 205 is advanced so that the distal tip of the catheter 205 lies at a distal-most extent of the length of blood vessel where embolic material 215 will be provided. To deploy the retention elements 210, 211 and the embolic material 215, the catheter 205 is retracted over the pushrod 206, preventing retraction of the retention elements 210, 211 and the embolic material 215. Both the retention elements 210, 211 and the embolic material 215 are preferably capable of radial expansion, allowing the occlusion of blood vessels having inner diameters larger than the bore of the catheter 205. After the catheter 205 is retracted and the retention elements 210, 211 and the embolic material is positioned, the pushrod 206 can be retracted and the catheter 205 removed. As above, the delivery system 200 is particularly useful in embolization procedures for the treatment of hemorrhage, in which the distal end of the catheter is positioned so that the embolic material will span a length of the blood vessel that includes a disruption in its wall.

In addition to deployment by retraction of the catheter, the retentive elements 210, 211 and the embolic material 215 can be pushed out of the distal end of the catheter 205 by advancing the pushrod 206 distally.

The catheter 205 is provided in multiple sizes, including without limitation 5 French (1.667 mm or 0.066") which is suitable for treating larger structures such as varioceles, 0.027" (0.69 mm) inner diameter, and 0.021" (0.53 mm) inner diameter, which may be used to embolize sites of bleeding in the gastrointestinal tract, splenic aneurysms, and the like.

The distal retention element 211 can have a shape similar to the shapes described for retention element 115 above and shown in FIG. 2, but can also be tapered or football shaped. Together with the proximal retention element 210, the distal retention element 211 spatially constrains the embolic material, limiting its migration within the blood vessel.

The embolic material 215 is preferably made of a superabsorbent polymer which absorbs water from the bloodstream to expand to fill the vessel lumen, including without limitation compressed collagen. The embolic material 215 can also include a rigid spacing element (not shown) made of, e.g., nitinol to ensure that the plug retains a fixed length. The spacing element can be attached, in some cases, to one or both of the retention elements 210, 211. Devices of the invention can come in any number of sizes (lengths, diameters) for use in a variety of applications including trauma, varicocele, pelvic congestion syndrome, peripheral aneurysm, gastrointestinal bleeding, etc. Devices of the invention can also be used in both arterial and venous systems.

The delivery systems of the invention, and their various components, are made using materials and techniques that are well established in the field. For instance, shape memory wires 110 and retentive elements 115, 210, 211 can be made by coiling or laser-cutting to shape and heat-setting. Catheter bodies can be made by extrusion or by means of coated mandrels, or any other suitable method.

Delivery systems according to these embodiments possess several advantages relative to the current state of the art. First, these devices allow rapid, one-step deployment of liquid embolics and, simultaneously, of retentive structures that reduce or even prevent migration of the liquid embolics beyond the site of deployment. These devices require only a single catheter and single intervention, promoting shorter procedure times, and are made using low cost, common materials that are known to those of skill in the medical implant and catheter fields. Additionally, the volume of the liquid embolic applied can be controlled finely by the user at the time of deployment, allowing systems and methods of the present invention to embolize a range of vessel volumes and sizes without the need for significant customization or alteration.

The phrase "and/or," as used herein should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "consists essentially of" means excluding other materials that contribute to function, unless otherwise defined herein. Nonetheless, such other materials may be present, collectively or individually, in trace amounts.

As used in this specification, the term "substantially" or "approximately" means plus or minus 10% (e.g., by weight or by volume), and in some embodiments, plus or minus 5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

Certain embodiments of the present invention have described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A system for treating a patient, the system comprising:
   a catheter;
   at least one retention element slidably disposed within the catheter;
   an embolic material flowable or slidable through a lumen of the catheter; and
   an elongate body connected to the at least one retention element;
   wherein the elongate body further comprises a detachable link, the detachable link being one of an electrolytically severable segment, a mechanical link, and a thermally severable segment; and
   wherein the at least one retention element is configured to move from an unexpanded configuration to an expanded configuration within a body lumen and retain the embolic material substantially proximal to the at least one retention element within the body lumen.

2. The system for treating a patient of claim 1, wherein the detachable link is disposed between a portion of the elongate body connected to the at least one retention element and another portion of the elongate body.

3. The system of claim 1, wherein the elongate body is a shape memory wire.

4. The system of claim 1, wherein the at least one retention element is moveable between the unexpanded configuration characterized by a first diameter and the expanded configuration characterized by a second diameter larger than the first diameter.

5. The system of claim 1, wherein the at least one retention element comprises a spiral shape.

6. The system of claim 1, wherein the at least one retention element comprises a plurality of cross-members.

7. The system of claim 1, wherein the at least one retention element has a substantially planar structure.

8. A method of treating a patient utilizing a system according to claim 1, the method comprising:
   inserting a distal end of the catheter into a blood vessel;
   advancing the at least one retention element distally from the catheter into the blood vessel; and
   disposing the embolic material substantially proximally to the at least one retention element through the catheter.

9. A system for treating a patient, the system comprising:
   a catheter;
   an embolic material slidably disposed within a lumen of the catheter;
   a first retention element and a second retention element disposed proximally and distally about the embolic material, respectively;
   a pushrod comprising an elongate body slidably disposed within the catheter; and
   a link disposed on an end of the pushrod, the link detachably connecting the end of the pushrod to the first retention element, the link being one of an electrolytically severable segment, a mechanical link, and a thermally severable segment;
   wherein the second retention element is configured to move from an unexpanded configuration to an expanded configuration within a body lumen and retain the embolic material substantially proximal to the second retention element within the body lumen.

10. The system of claim 9, wherein the link is a shape memory wire.

11. The system of claim 9, wherein the embolic material absorbs water when disposed in an aqueous environment.

12. The system of claim 9, wherein the embolic material forms a gel.

13. The system of claim 9, wherein the first retention element and the second retention element are connected to one another by an elongate member extending between them.

14. The system of claim 9, wherein the embolic material is a superabsorbent polymer plug.

15. The system of claim 14, wherein the superabsorbent polymer plug includes collagen.

16. A method of treating a patient using the system of claim 9, the method comprising the steps of:
inserting a distal end of the catheter into a blood vessel of a patient; and
retracting the catheter over the pushrod, thereby releasing the first retention element and the second retention element and the embolic material.

17. A method of treating a patient, comprising the steps of:
forming, in a body lumen of a patient, an occlusive structure comprising:
an expandable implant configured to move from an unexpanded configuration to an expanded configuration within the body lumen;
a polymer plug contacting the expandable implant; and
an elongate body connected to the expandable implant;
wherein the elongate body further comprises a detachable link, the detachable link being one of an electrolytically severable segment, a mechanical link, and a thermally severable segment;
wherein the polymer plug is formed by a liquid embolic material or a superabsorbent polymer material; and
wherein the expandable implant is configured to retain the polymer plug substantially proximal to a distalmost end of the expandable implant within the body lumen.

18. The method of claim 17, wherein the expandable implant includes a proximal radially expandable element and a distal radially expandable element connected by at least a portion of the elongate body and the polymer plug is a superabsorbent polymer contacting the elongate body between the proximal and distal radially expandable elements.

19. The method of claim 17, wherein the expandable implant is a single radially expandable element and the polymer plug is a hardened liquid embolic material contacting the radially expandable element.

20. The method of claim 17, wherein the detachable link is disposed on the elongate body between a portion of the elongate body connected to the expandable implant and another portion of the elongate body.

* * * * *